United States Patent [19]

Lindberg et al.

[11] 4,177,291

[45] Dec. 4, 1979

[54] COMPOUNDS HAVING ANTIDEPRESSIVE ACTIVITY

[75] Inventors: Ulf H. A. Lindberg; Svante B. Ross, both of Södertälje; Seth O. Thorberg, Järna; Sven O. Ögren, Södertälje, all of Sweden

[73] Assignee: Astra Läkemedel Aktiebolag, Södertälje, Sweden

[21] Appl. No.: 827,085

[22] Filed: Aug. 23, 1977

[30] Foreign Application Priority Data

Aug. 25, 1976 [SE] Sweden .................................. 7609385

[51] Int. Cl.$^2$ .......................... A01N 9/20; A01N 9/24; C07C 97/10

[52] U.S. Cl. ................................ 424/330; 260/326 R; 260/465 D; 260/465 G; 260/501.17; 260/501.19; 424/316

[58] Field of Search ..................... 260/570.5 C, 501.17; 424/316, 330

[56] References Cited

U.S. PATENT DOCUMENTS 3,278,600   10/1966   L'Italien ............................ 260/570.5

3,819,706   6/1974   Mehta ................................ 260/570.5

FOREIGN PATENT DOCUMENTS 898010   6/1962   United Kingdom .................. 260/570.5

Primary Examiner—Robert V. Hines
Attorney, Agent, or Firm—Brumbaugh, Graves, Donohue & Raymond

[57] ABSTRACT

A compound of the formula

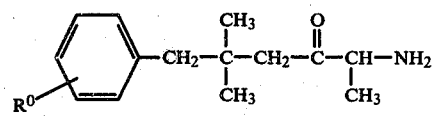

or a pharmaceutically acceptable acid addition salt thereof, in which formula the group $R^0$ is selected from the group consisting of hydrogen, chlorine, bromine, methyl, trifluoromethyl and methoxy.

Pharmaceutical compositions containing these compounds are useful for treatment of depressive disorders.

15 Claims, No Drawings

COMPOUNDS HAVING ANTIDEPRESSIVE ACTIVITY

This invention relates to new aminoketones and processes for their preparation. This invention also relates to methods for the pharmacological use of these compounds and to pharmaceutical preparations containing such compounds.

An object of this invention is to provide compounds having effect on the central nervous system, especially antidepressive activity, and having a reduced frequency of side effects and increased effectiveness compared to drugs presently used in this area.

A further object of this invention is to provide pharmaceutical preparations containing as active ingredient a compound according to this invention.

Still an object of this invention is to provide methods for the treatment of depressive disorders.

The presently most used compound for controlling depressions is imipramine (Tofranil ®)

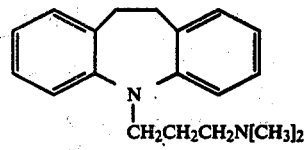
CH$_2$CH$_2$CH$_2$N[CH$_3$]$_2$

This compound is both mood elevating and psychomotor activating, but it possesses several disadvantages. It is anticholinergic and causes anticholinergic symptoms such as dryness of the mouth, tremor, tachycardia and sweating. In higher doses it can provoke serious heart arrhythmias and in normal doses it can cause toxic interactions in persons with heart failures. Furthermore, another drawback with treatment with imipramine is the late onset of the antidepressive effect, which effect is observable first after about 3 weeks of treatment.

It has been shown that imipramine has an effect on the action of the transmitter substances in the central nervous system. More specifically, imipramine inhibits the re-uptake mechanism of noradrenaline (NA) and 5-hydroxytryptamine (5-HT). The mood elevation part of the antidepressive action is assumed to be mainly related to the inhibition of 5-HT uptake.

According to the present invention we have found that certain new compounds can be used for inhibiting selectively the central neuronal uptake of 5-hydroytryptamine. Further the heart toxicities for these new compounds are considerably weaker than those of imipramine.

The new compounds according to the invention can be described by the general formula

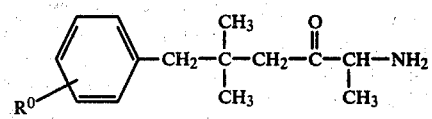
(I)

in which formula R° is selected from the group consisting of hydrogen, chlorine, bromine, methyl, trifluoromethyl and methoxy, including pharmaceutically acceptable acid-addition salts thereof.

Since these new compounds contain an asymmetric carbon atom, they exist in the form of optically active forms, and can be resolved into their optical antipodes by well known methods such as by using optically active acids such as tartaric acid, camphor-10-sulphonic acid, dibenzoyl tartaric acid, and the like.

A preferred subgroup of compounds within the invention is obtained when, in the formula I above, the group R° is placed in para-position. A further preferred subgroup of compounds is obtained when the group R° is selected from chlorine, bromine and methyl. A particularly preferred subgroup is obtained when the group R° is placed in para-position, and is selected from chlorine, bromine and methyl.

The following compounds can be mentioned as examples of compounds included in the invention:

2-Amino-6-(4-chlorophenyl)-5,5-dimethyl-3-hexanone

2-Amino-6-(4-bromophenyl)-5,5-dimethyl-3-hexanone

2-Amino-6-(4-methylphenyl)-5,5-dimethyl-3-hexanone

2-Amino-6-(3-methylphenyl)-5,5-dimethyl-3-hexanone

2-Amino-6-phenyl-5,5-dimethyl-3-hexanone.

The compounds of the present invention can be prepared by the Gabriel reaction, i.e. by reacting a compound of the formula

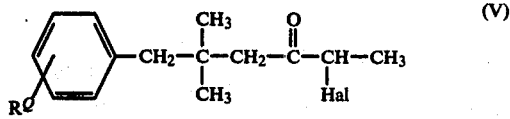
(V)

in which formula Hal is Cl or Br, with a phthalimide salt (preferably potassium pthalimide) to the formation of a compound of the formula

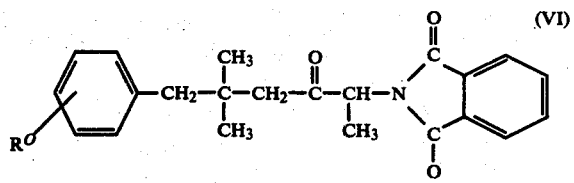
(VI)

followed by hydrolysing said compound to produce the compound of the formula

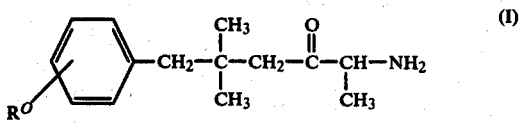
(I)

in which formulas R° is selected from hydrogen, chlorine, bromine, methyl, trifluoromethyl and methoxy.

The intermediate of the formula V can be prepared according to the following reaction scheme:

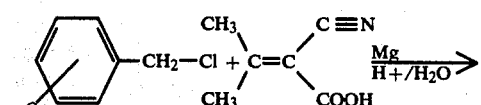

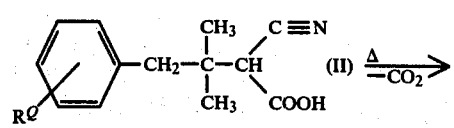
(II)

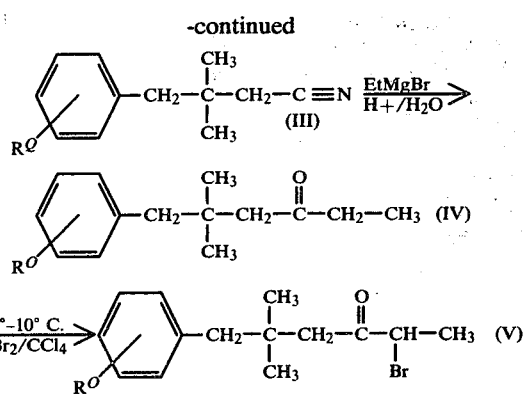

The intermediates of the formulas II–VI are novel compounds and constitute a further aspect of the invention.

The new compounds of the formula I may be used therapeutically as the racemic mixtures of (+)- and (−)- forms, which in the usual case are obtained at the synthesis. They may also be resolved by methods known per se into the corresponding optically active modifications which, likewise, may be used in therapy. If desired, the optically active modification may be prepared by way of direct synthesis, e.g. via an optically active compound of the formula V.

(b) Pharmaceutical preparations

In clinical practice the compounds of the present invention will normally be administered orally, rectally or by injection, in the form of pharmaceutical preparations comprising the active ingredient either as a free base or as a pharmaceutically acceptable non-toxic, acid addition salt, e.g. the hydrochloride, hydrobromide, lactate, acetate, phosphate, sulphate, sulphamate, citrate, tartrate, oxalate and the like in association with a pharmaceutically acceptable carrier. Accordingly, terms relating to the novel compounds of this invention, whether generically or specifically, are intended to include both the free amine base and the acid addition salts of the free base, unless the context in which such terms are used, e.g. in the specific examples, would be inconsistent with the broad concept. The carrier may be a solid, semisolid or liquid diluent or capsule. These pharmaceutical preparations constitute a further aspect of this invention. The active substance should constitute between 0.1 and 95% by weight of the composition, preferably between 0.5 and 10% by weight for preparations intended for injection and between 2 and 50% by weight for preparations suitable for oral administration.

To produce pharmaceutical preparations containing a compound ot the invention in the form of dosage units for oral application the selected compound, may be mixed with a sold pulverulent carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g., gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compounds.

For the preparation of soft gelatine capsules (pearl-shaped closed capsules) consisting of gelatine and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil. Liquid preparations for oral application may be in the form of syrups or suspensions, for example, solutions containing from about 2% to about 20% by weight of the active substance herein described, the balance being for example sugar and a mixture of ethanol, water, glycerol and propyleneglycol. Optionally such liquid preparations may contain colouring agents, flavouring agents, saccharine and carboxymethyl cellulose as a thickening agent.

Solutions for parenteral applications by injection can be prepared in the form of an aqueous solution of a water-soluble pharmaceutically acceptable acid addition salt of the active substance, preferably in a concentration of from about 0.5% to about 10% by weight. These solutions may also contain stabilizing agents and/or buffering agents and may conveniently be provided in various dosage unit ampoules.

Suitable daily doses of the compounds of the invention at therapeutical treatment is 100 to 500 mg at peroral administration and 20 to 100 mg at parenteral administration.

The preferred compound of the invention has the formula

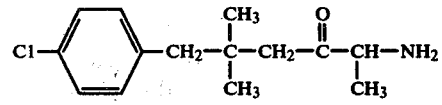

Preferably this compound is prepared and used in the form of its hydrochloride salt.

The preparation of compounds according to the invention is illustrated by the following example.

EXAMPLE 1.

Preparation of 2-amino-6-(4-chlorophenyl)-5,5-dimethyl-3-hexanone

2-Cyano-3,3-dimethyl-4-(4-chlorophenyl)-butyric acid was prepared according to the method for the analogue without chlorine in the ring [JACS 76 1911 (1954), Prout, F.S. et al.]. The yield of recrystallized substance was 66%. M.p. 137°–138° C. (white needles from trichloroethylene).

The cyanoacid was decarboxylated in a flask heated at 170° C. with stirring and collection of the theoretical amount of carbon dioxide (4 hours) over water. The product was distilled at 163°–164° C./9.5 mm Hg affording 4-(4-chlorophenyl)-3,3-dimetylbutyronitrile as a colourless oil. Yield: 87%.

The nitrile (59.0 g; 0.284 mole) was dissolved in dry ether (300 ml) and added during 20 minutes to a freshly prepared suspension of ethylmagnesiumbromide (0.711 mole) in dry ether (500 ml) whereby a spontaneous reflux was obtained. Heating the mixture under reflux was continued over night. The reaction mixture was poured into ice (2000 ml) and concentrated hydrochloric acid (800 ml) under vigorous stirring. The stirring was continued for 4 hours, the ether was separated and the acid phase extracted with ether. The combined ether phase was washed with water and dried over anhydrous sodium sulphate. The ether was evaporated under vacuum and the remaining oil was distilled at 112°–114° C./0.5 mm Hg affording the 5,5-dimethyl-6-(4-chlorophenyl)-3-hexanone (56.2 g; 83% yield) as a colourless oil.

The ketone (20.0 g; 0.084 mole) was dissolved in carbontetrachloride (200 ml). The solution was cooled on ice and a 10% solution of bromine (0.084 mole) in CCl$_4$ was added at such a rate that the drops were decolourized immediately. The total time of bromination was about 2 hours. After evaporation of the solvent in vacuo a pure oil of 2-bromo-5,5-dimethyl-6-(4-chlorophenyl)-3-hexanone (26.5 g; 99% yield) was obtained. To a solution of the bromoketone (5.0 g; 0.016 mole) in dimethylformamide (20 ml) was added potassium phtalimide (3.2 g; 0.017 mole) in portions under stirring during 5 minutes. The temperature was raised spontaneously to 40° C. Stirring was continued for 15 minutes. Chloroform (30 ml) was added and the mixture was poured into water (100 ml) under stirring. The organic layer was separated and the aqueous phase was washed with CHCl$_3$. The combined chloroform phase was washed with 0.2 N sodium hydroxide solution and water. After drying over anhydrous sodium sulphate and evaporation of the solvent a yellow oil was obtained. The oil crystallized from ethanol-ether affording white crystals of 6-(4-chlorophenyl)-5,5-dimethyl-2-phtalimido-3-hexanone (2.6 g; 43% yield) melting at 96°–98° C.

The phtalimido compound (12.0 g; 0.034 mole) was hydrolyzed by boiling in a mixture of concentrated hydrobromic acid (25 ml) and glacial acetic acid (25 ml) during 40 hours. The solution was cooled on ice and the precipitated phtalic acid was filtered off.

The filtrate was evaporated (50° C./10 mm Hg) till it was almost dry. The residue was dissolved in water and the brown solution was washed three times with ether. After making the solution alkaline with 5 N ammonia, the aminoketone was taken up in large volumes of ether. To the combined ether phase was added diluted hydrochloric acid. The acid phase was evaporated under addition of absolute ethanol. The residue was a viscous yellow oil which crystallized by the addition of dry ether. After recrystallization from hexane-isopropanol, white crystals of 2-amino-6-(4-chlorophenyl)-5,5-dimethyl-3-hexanone hydrochloride was obtained. Melting point: 120°–122° C. Yield: 69%

Pharmacological methods

A. Biochemical tests

1. Inhibition of the uptake of carbon-14 5-HT and tritiated noradrenaline in vitro and in vivo The method is described by Ross, Renyi and Ogren in European Journal of Pharmacology 17 (1972), 107–112. Tricyclic antidepressant drugs of type imipramine added in vitro or given in vivo to mice decrease the uptake of $^{14}$C-5-HT and $^3$H-NA in vitro. In the in vitro experiments different concentrations of the test compound were added to the incubation medium. In the in vivo experiments different doses of the test drug were administered intraperitoneally half an hour before the animals were killed. The incubation performance was the same in the two types of experiments, i.e. the midbrain was taken out and sliced and incubated in a mixture consisting of, per 100 mg of brain slices, 0.2 n-mole of $^{14}$C-5-HT, 0.2 n-mole of $^3$H-NA and 11μ mole of glucose in 2 ml of Krebs-Henseleit buffer, pH 7.4. The incubation time was 5 minutes. The radioactive amines taken up in the slices were dissolved in Soluene-350 ® (Packard) and the amounts were determined with the double labelling technique by liquid scintillation. The concentration or dose producing 50 percent decrease of the active uptake (ED$_{50}$) was determined graphically from dose response curves. Active uptake is defined as that part of the radioactive uptake which is inhibited by a high concentration of cocaine. All doses were given at least to four animals.

B. Pharmacological tests 1. 5-HTP response potentiation test

Inhibition of the uptake of 5-HT potentiates the effects of administered 5-hydroxytryptophan (5-HTP) probably by increasing the amount of 5-HT at the receptor. Three mice are given the test drugs one hour (or 4, 24 hours) before dl-5-HTP 90 mg/kg i.v. 5-HTP alone gives only a weak behavioural syndrome but in pretreated mice there is seen a characteristic behavioural syndrome, which comes within five minutes: tremor, lordosis, abduction of the hindlegs, head-twiches. The strength of the syndrome is scored from 0 to +3. Each group consists of 3 animals and at least 4 groups were tested at 25 mg/kg i.p. Control groups receiving imipramine (Tofranil ®) are used as reference, since imipramine constantly potentiated dl-5-HTP. The least dose of the test compound producing maximal score (+3) in all animals is estimated from a logarithmic dose-response curve, and is denoted "effective dose" in the following Table.

The result from the above described tests are summarized in the following Table. The code number GEA 995 represents the compound 2-amino-6-(4-chlorophenyl)-5,5-dimethyl-3-hexanone hydrochloride, i.e. a compound according to the invention.

Table

| | Inhibition (50%) of uptake | | Potentiation of 5- |
|---|---|---|---|
| | in vitro | in vivo | |
| Compound | 5-HT[1] NA[2] (μg/ml) | 5-HT[1] NA[2] (mg/kg i.p.) | HPT[n] effective dose (mg/kg i.p.) |
| GEA 995 | 0.6  >10 | 20 > 40 | 4 |
| Imipramine | 0.1  0.06 | 24  6 | 15 |

[1]5-HT = 5-hydroxydryptamine, 1 + 10$^{-7}$M
[2]NA = 1-noradrenaline, 1 + 10$^{-7}$M
[3]5-HTP = 5-Hydroxytryptophan
i.p. = intraperitoneal administration (1) 5-HT=5-hydroxytryptamine, 1×10$^{-7}$M
(2) NA=1-noradrenaline, 1×10$^{-7}$M
(3) 5-HTP=5-Hydroxytryptophan
i.p.=intraperitoneal administration Evaluation of the results obtained in the pharmacological tests The tested compound according to the invention block the uptake of 5-hydroxytryptamine in brain in vivo and in vitro, but does not inhibit the uptake of noradrenaline. In vivo it is more potent than imipramine as inhibitor of the 5-hydroxytryptamine. Moreover, it potentiates the responses of 5-hydroxytryptophan at considerably lower doses than imipramine. These results indicate that the new compounds are much more selective than imipramine in inhibiting the uptake of 5-hydroxytryptamine.

Pharmaceutical compositions

The following examples illustrates the preparation of pharmaceutical compositions according to the invention. For the preparation of tablets the following compositions were made

| | |
|---|---|
| (a) 2-Amino-6-(4-chlorophenyl)-5,5-dimethyl-3- | |
| hexanone hydrochloride | 50 g |
| Lactose | 85 g |
| Potatoe starch | 40 g |
| Polyvinylpyrrolidone 5 g | |
| Cellulose Avicel | 18 g |
| Magnesium stearate | 2 g |
| (b) 2-Amino-6-(4-chlorophenyl)-5,5-dimethyl-3- | |
| hexanone hydrochloride | 100 g |
| Lactose | 90 g |
| Potatoe starch | 50 g |
| Polyvinylpyrrolidone | 5 g |
| Cellulose Avicel | 23 g |
| Magnesium stearate | 2 g |

From the above compositions 1000 tablets were made, containing 50 mg and 100 mg of active substance, respectively. If desired, the obtained tablets can be film coated with e.g. methyl cellulose in an organic solvent.

We claim:

1. A compound of the general formula

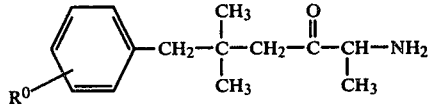 (I)

or a pharmaceutically acceptable acid addition salt thereof, in which formula the group R° is selected from the group consisting of hydrogen, chlorine, bromine, methyl, trifluoromethyl and methoxy.

2. A compound according to claim 1, in which formula the group R° is selected from the group consisting of chlorine, bromine and methyl.

3. A compound according to claim 1, in which formula the group R° is placed in para-position and is selected from the group consisting of chlorine, bromine and methyl.

4. A compound according to claim 1, of the formula

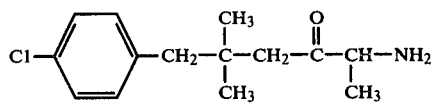

or a pharmaceutically acceptable acid addition salt thereof.

5. A compound according to claim 1 in the form of an optically pure isomer.

6. A pharmaceutical composition which effects selective inhibition of central neuronal uptake of 5-hydroxytryptamine, comprising as the active ingredient, between 0.1 and 95% by weight of said composition, a compound according to claim 1, together with a pharmaceutically acceptable carrier for use in the treatment of depressive disorders related to neuronal uptake of 5-hydroxytryptamine.

7. A method for the treatment of depressive disorders related to neuronal uptake of 5-hydroxytryptamine, comprising the administration to a host in need of such treatment of a therapeutically effective amount of a compound according to claim 1 which effects selective inhibition of central neuronal uptake of 5-hydroxytryptamine.

8. A pharmaceutical composition according to claim 6 wherein the R° group of the active ingredient is selected from the group consisting of chlorine, bromine and methyl.

9. A pharmaceutical composition according to claim 8, wherein the R° group of the active ingredient is in the para-position.

10. A pharmaceutical composition according to claim 6, wherein the active ingredient is a compound having the structural formula

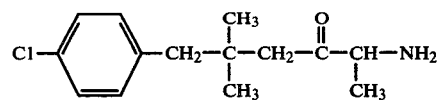

and a pharmaceutically acceptable addition salt thereof.

11. A pharmaceutical composition according to claim 6 wherein the active ingredient is in the form of an optically pure isomer.

12. A method of treatment according to claim 7 wherein the R° group of the compound administered is selected from the group consisting of chlorine, bromine and methyl.

13. A method of treatment according to claim 12 wherein the R° group of the compound administered is in the para-position.

14. A method of treatment according to claim 7 wherein the compound administered has the structural formula

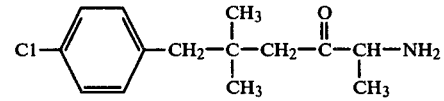

and a pharmaceutically acceptable addition salt thereof.

15. A method of treatment according to claim 7, wherein the compound administered is in the form of an optically pure isomer.

* * * * *

UNITED STATES PATENT AND TRADEMARK OFFICE
CERTIFICATE OF CORRECTION

PATENT NO. : 4,177,291
DATED : December 4, 1979
INVENTOR(S) : Ulf Henrik Anders Lindberg et al.

It is certified that error appears in the above—identified patent and that said Letters Patent is hereby corrected as shown below:

Column 2, lines 42-44, "$\overset{\text{C}}{\underset{\text{O}}{|}}$" should read -- $\overset{\text{C}}{\underset{\text{O}}{\parallel}}$ --.

Column 3, line 54, after "compound" delete the comma.

Column 3, line 55, "sold" should read -- solid --.

Column 6, line 52, "5-HT$^1$ NA$^2$" both instances should read -- 5-HT$^{1)}$ NA$^{2)}$ --.

Column 6, line 52, HTP$^n$" should read -- HTP$^{3)}$ --.

Column 6, line 55, "6" should appear under the "40" in the preceding line.

Column 6, delete lines 60-63.

Column 7, line 20, "5 g" should appear directly under "40 g" in the preceding line.

Signed and Sealed this

Twenty-ninth Day of April 1980

[SEAL]

Attest:

SIDNEY A. DIAMOND

Attesting Officer    Commissioner of Patents and Trademarks